US007776860B2

(12) United States Patent
Bakker

(10) Patent No.: US 7,776,860 B2
(45) Date of Patent: *Aug. 17, 2010

(54) PROCESS FOR THE PREPARATION OF 3-AMINO-8-(1-PIPERAZINYL)-2H-1-BENZOPYRAN-2-ONE AND SALTS AND SOLVATES THEREOF

(75) Inventor: Cornelis Bakker, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 844 days.

This patent is subject to a terminal disclaimer.

(21) Appl. No.: 11/085,136

(22) Filed: Mar. 22, 2005

(65) Prior Publication Data

US 2005/0215566 A1    Sep. 29, 2005

Related U.S. Application Data

(60) Provisional application No. 60/555,958, filed on Mar. 25, 2004.

(51) Int. Cl.
*A61K 31/497* (2006.01)
*C07D 241/04* (2006.01)
*C07D 295/00* (2006.01)

(52) U.S. Cl. .................... 514/252.12; 544/358
(58) Field of Classification Search .......... None
See application file for complete search history.

(56) References Cited

U.S. PATENT DOCUMENTS

| | | | |
|---|---|---|---|
| 5,009,895 A | 4/1991 | Lui | |
| 5,194,437 A | 3/1993 | Peligon et al. | |
| 5,478,572 A | 12/1995 | David et al. | |
| 6,010,717 A | 1/2000 | Arends-Scholte et al. | |
| 6,312,717 B1 | 11/2001 | Molinoff et al. | |
| 6,767,921 B2 * | 7/2004 | Capet et al. | 514/464 |
| 2002/0156075 A1 | 10/2002 | Childers et al. | |
| 2002/0183938 A1 | 12/2002 | Kobylecki et al. | |
| 2003/0190353 A1 | 10/2003 | Oosterbaan et al. | |
| 2004/0014769 A1 | 1/2004 | Welch et al. | |
| 2005/0215551 A1 * | 9/2005 | Bakker et al. | 514/235.5 |
| 2005/0215567 A1 * | 9/2005 | Bakker et al. | 514/254.11 |

FOREIGN PATENT DOCUMENTS

| | | |
|---|---|---|
| EP | 0 189 612 | 8/1986 |
| EP | 0 372 657 | 6/1990 |
| EP | 0 490 772 | 6/1992 |
| EP | 0 533 268 | 3/1993 |
| EP | 0 650 964 A1 | 5/1995 |
| WO | WO 93/13766 | 7/1993 |
| WO | WO 96/09815 | 4/1996 |
| WO | WO 97/36893 | 10/1997 |
| WO | WO 98/42344 | 10/1998 |
| WO | WO 99/52907 | 10/1999 |
| WO | WO 00/39128 | 7/2000 |
| WO | WO 02/18367 | 3/2002 |

OTHER PUBLICATIONS

Anand, "Neurotrophic Factors and their Receptors in Human Sensory Neuropathies," *Prog. Brain Res.*, 146, 477-492 (2004).
Christianson et al., "Beneficial Effects of Neurotrophin Treatment on Diabetes-induced Hypoalgesia in Mice," *J. Pain*, 4, 493-504 (2003).
Kataoka et al., "Potent Inhibitors of Acyl-CoA:Cholesterol Acyltransferase. Structure—Activity Relationships of Novel N-(4-Oxochroman-8-yl)amides," *J. Med. Chem.* 38:3174-3186 (1995).
Wang et al., "Glial Cell-derived Neurotrophic Factor Normalizes Neurochemical Changes in Injured Dorsal Root Ganglion Neurons and Prevents the Expression of Experimental Neuropathic Pain," *Neuroscience* 121:815-824 (2003).
International Search Report for PCT/EP2005/051326 (counterpart).
Copending U.S. Appl. No. 11/079,089, filed Mar. 15, 2005.
International Search Report for PCT/EP2005/051328, dated Sep. 14, 2005.
Nicholson et al., "5-hydroxytryptamine (5-HT, serotonin) and Parkinson's disease—opportunities for novel therapeutics to reduce the problems of levodopa therapy," European Journal of Neurology, 2002, 9 (Suppl. 3), pp. 1-6.
Office Action dated Apr. 15, 2009, in U.S. Appl. No. 11/079,089.

(Continued)

*Primary Examiner*—James O Wilson
*Assistant Examiner*—Noble Jarrell
(74) *Attorney, Agent, or Firm*—Finnegan, Henderson, Farabow, Garrett & Dunner, L.L.P.

(57) ABSTRACT

The invention relates to a novel process for the preparation of 3-amino-8-(1-piperazinyl)-2H-1-benzopyran-2-one, a broad spectrum 5-HT receptor binding ligand having potent $5\text{-HT}_{1A}$-agonistic as well as $5\text{-HT}_{1D}$-antagonistic activity. The invention also relates to novel salts and solvates, in particular hydrates of salts of said compound, as well as to their use as medicaments.

The invention relates the compounds with the formula (7)

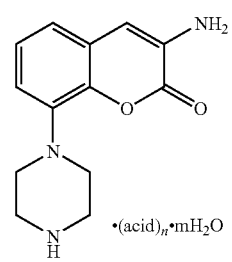

(7)

6 Claims, No Drawings

OTHER PUBLICATIONS

Office Action dated Apr. 29, 2009, in U.S. Appl. No. 11/178,309.
Office Action dated Feb. 12, 2008, in U.S. Appl. No. 11/085,193.
Office Action dated Jul. 22, 2008, in U.S. Appl. No. 11/085,193.
Office Action dated Sep. 15, 2008, in U.S. Appl. No. 11/085,136.
Copending U.S. Appl. No. 11/085,193, filed Mar. 22, 2005.
Copending U.S. Appl. No. 11/178,309, filed Jul. 12, 2005.
Fuji et al., "New Tetrahydrobenzimidazole Derivatives Are Serotonin-7 Binding Agents Useful for Treating, e.g., Mental Diseases," Derwent Abstract, XP-002337215 of WO 02/18367 (2002).
Office Action dated Aug. 10, 2007, in U.S. Appl. No. 11/085,193.

* cited by examiner

PROCESS FOR THE PREPARATION OF 3-AMINO-8-(1-PIPERAZINYL)-2H-1-BENZOPYRAN-2-ONE AND SALTS AND SOLVATES THEREOF

CROSS REFERENCE TO RELATED APPLICATION

This application claims the benefit of U.S. Provisional Application No. 60/555,958, filed Mar. 25, 2004, the content of which is incorporated herein by reference.

FIELD OF THE INVENTION

The invention relates to a novel process for the preparation of 3-amino-8-(1-piperazinyl)-2H-1-benzopyran-2-one, a broad spectrum 5-HT receptor binding ligand having potent $5\text{-HT}_{1A}$-agonistic as well as $5\text{-HT}_{1D}$-antagonistic activity. The invention also relates to novel salts and solvates, in particular hydrates of salts of said compound.

The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which serotonin receptors are involved, or that can be treated via manipulation of those receptors.

BACKGROUND OF THE INVENTION

The protagonist of the present invention, 3-amino-8-(1-piperazinyl)-2H-1-benzopyran-2-one, is known as its hydrochloric acid salt. As such it is described as 'example 8' in EP 0650 964. Despite the fact that the synthetic route as outlined in said patent has quite an acceptable yield, it is definitely not suited for synthesis on the scale required for a drug in clinical development, let alone the scale required for a marketed drug. The problems with the original synthesis are manifold. First, the key starting material, 3-nitro-2-hydroxybenzaldehyde is not available on a commercial scale, and was prepared by nitration of 2-hydroxybenzaldehyde, resulting in a mixture of 3- and 5-nitro-2-hydroxybenzaldehyde which can only be separated by relatively complicated chromatographic methods. The second step, an Erlenmeyer condensation, results in a very viscous mixture which is hard to stir on a technical scale, and from which the isolation of the desired product appeared difficult as well. The third step, the reduction of the nitro group to the amine, using Fe/HCl is laborious, and the isolation of the reaction product from the large amount of rust ($Fe_2O_3$) appeared to be next to impossible on a technical scale. In step 4 the potential carcinogen N-benzyl-bis-chloroethylamine was used. Large scale use of such compounds creates insurmountable safety hazards. After acidic amide hydrolysis (step 5) the end product is contained in a large amount of a mixture of acetic and sulphuric acid. This mixture was neutralized using solid sodium bicarbonate, a laborious task. After the isolation, the crude product had to be purified by chromatography, because the acidic hydrolysis produced a structurally closely related 3-hydroxycoumarin derivative as byproduct. In conclusion: all reaction steps of the synthetic route as outlined in EP 0650 964 show major problems when translated into a pilot scale production of several kilograms of the compound.

SUMMARY OF THE INVENTION

The goal of the present invention was to overcome the abovementioned problems, in order to be able to deliver kilogram quantities of the compound in a safe and economically feasible way.

The problems associated with the synthesis of 3-amino-8-(1-piperazinyl)-2H-1-benzopyran-2-one can be solved by the entirely new synthetic route according to the present invention, as summarized in the scheme below.

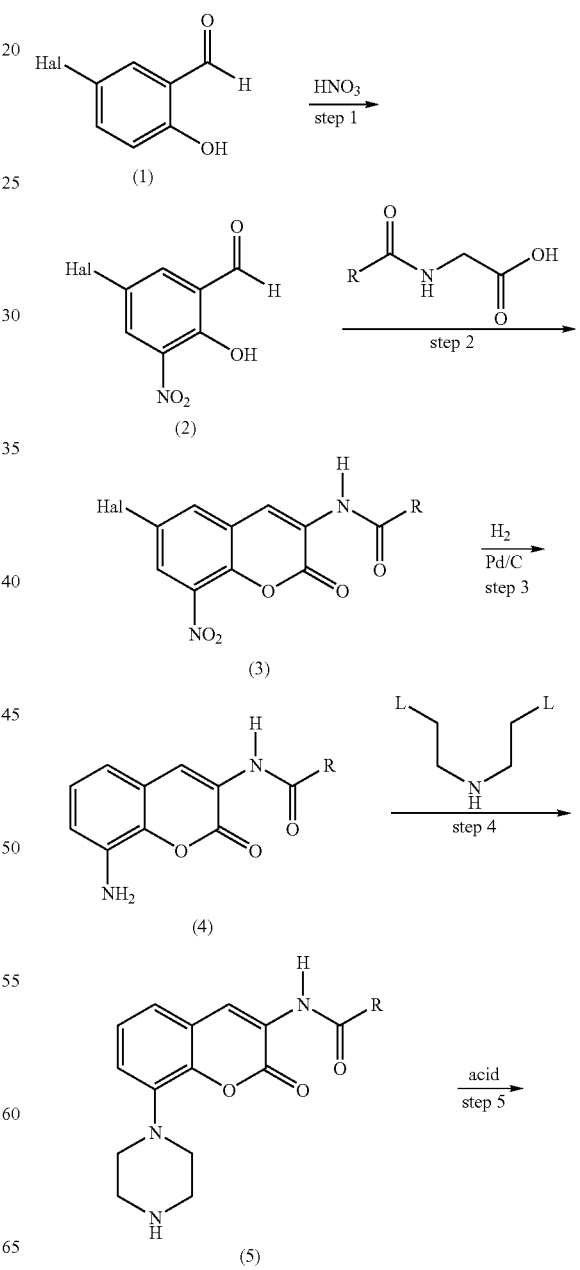

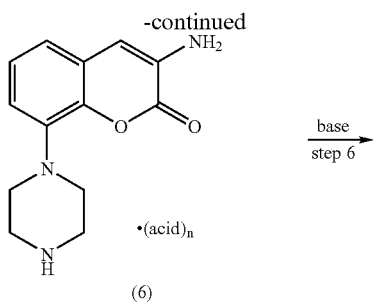

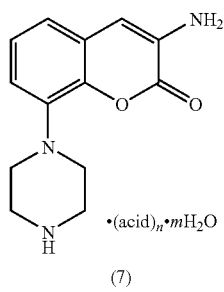

As a starting material a 5-halogen-2-hydroxybenzaldehyde (1) can be used, (e.g. the commercially available 5-bromo-2-hydroxybenzaldehyde), which can be selectively nitrated to yield 5-halogen-2-hydroxy-3-nitrobenzaldehyde (2), the intermediate necessary for the Erlenmeyer condensation leading to an N-(6-halogen-8-nitro-2-oxo-2H-1-benzopyran-3-yl) amide (3) which is subsequently reduced to an N-(8-amino-2-oxo-2H-1-benzopyran-3-yl) amide (4). Rather than using the potential carcinogen N-benzyl-bis-chloroethylamine, instead a compound of the general formula wherein L is a leaving group can be used to construct the piperazine ring. This results in an N-(8-(1-piperazinyl)-2-oxo-2H-1-benzopyran-3-yl-)amide (5). Hydrolysis of this amide using an acid results in (6). It is possible to neutralize this salt (6) to yield the free base, and to convert that into mono- or di-acid salts. However, it has surprisingly been found that partial neutralization of the tri-hydrochloric acid salt apparently directly results in the monohydrochloric acid salt. Titrimetric analysis shows that the product contains between 3.24 and 3.34 mmol HCl per gram of product, the latter value being exactly the theoretical value for the mono hydrochloric acid salt. 'Karl Fisher water assay titration' reveals that the product of the new synthetic route contains 6.2-6.5% (mass to mass) water, for all practical purposes indicative of a monohydrate, because the theoretical value is 6% water.

DETAILED DESCRIPTION OF THE INVENTION

In a first aspect the present invention relates to a process for the preparation of a compound of formula (7):

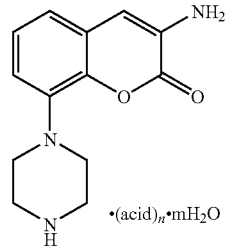

characterized in that a compound with formula (1):

wherein Hal is F, Cl, Br or I, is nitrated to yield 5-halogen-2-hydroxy-3-nitrobenzaldehyde (2), followed by an Erlenmeyer condensation of (2) with a glycine derivative of formula:

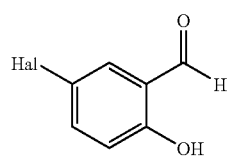

wherein R represents an alkyl($C_{1-6}$) or an aryl group to yield an N-(6-halogen-8-nitro-2-oxo-2H-1-benzopyran-3-yl) amide (3):

and a subsequent catalytic hydrogenation of (3) to yield an N-(8-amino-2-oxo-2H-1-benzopyran-3-yl)-amide (4),

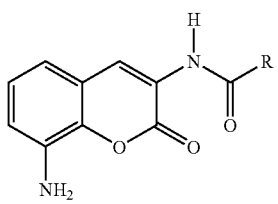
(4)

after which the obtained compound (4) is alkylated with a compound of the formula

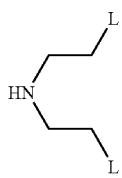

wherein L is a leaving group such as chloro, methanesulphonate or p-toluene-sulphonate, to yield an N-(8-(1-piperazinyl)-2-oxo-2H-1-benzopyran-3-yl-) amide (5),

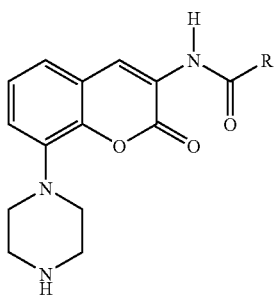
(5)

after which the amide function of (5) is hydrolyzed using an acid, resulting in the corresponding acid salt (6), in which n is 0, 1, 2 or 3.

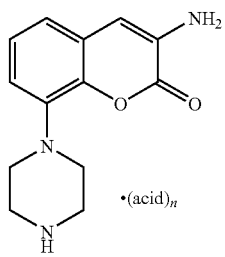
(6)

The compound of formula (6) is further (partially) neutralized to produce the product represented by formula (7)

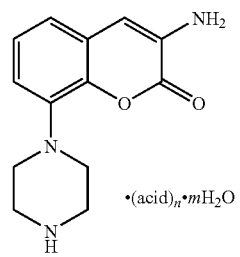
(7)

in which n and m independently can be 0, 1, 2 or 3.

The halogen group used in the starting material can be selected from F, Cl, Br and I. The preferred halogen group is Br.

Examples of a leaving group L are chloro, methanesulphonate and p-toluene-sulphonate. Preferable groups chloro and methanesulphonate. The most preferred leaving group is a chloro group.

R groups are either alkyl($C_{1-6}$) or aryl groups. In this description 'aryl' means furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazynyl, phenyl, indazolyl, indolyl, indolizinyl, isoindolyl, benzi[b]furanyl, benzo[b]thiophenyl, benzimidazolyl, benzthiazolyl, purinyl, quinolynyl, isochinolyl, chinolyl, phtalazinyl, quinazolinyl, quinoxalinyl, 1,8-naphthyridinyl, pteridinyl, naphthyl or azulenyl. Preferred R-groups are methyl and phenyl. Most preferred is methyl.

For step 5 inorganic and organic acids can be used. Examples of acids that can be used are inorganic acids such as hydrochloric acid, sulphuric acid, phosphoric acid and nitric acid, or with organic acids such as citric acid, fumaric acid, maleic acid, tartaric acid, acetic acid, trifluoro acetic acid, benzoic acid, p-toluene sulphonic acid, methanesulphonic acid and naphthalene sulphonic acid. The preferred acid in said step is hydrochloric acid.

Step 1 can be performed in acids. The preferred solvent is acetic acid. The reaction temperature is between 0° C. and 100° C., preferably about 60° C.

Step 2 can be performed in dipolar aprotic solvents. The preferred solvent is N-methyl-2-pyrrolidone. The reaction temperature is between 50° C. and 120° C., preferably about 60° C.

Step 3 can be performed in alcohols. The preferred alcohol is ethanol. The reaction temperature is between 20° C. and 100° C., preferably about 60° C.

Step 4 can be performed in organic solvents. The preferred solvent is monochlorobenzene. The reaction temperature is elevated when compared to room temperature, preferably the reaction is carried out at reflux.

Step 5 can be performed in alcohols. The preferred solvent is ethanol. The reaction temperature is between 20° C. and 100° C., preferably about 50° C.

Step 6 can be performed in alcohols. The preferred solvent is ethanol. Neutralisation is performed with a base in aqueous environment. The preferred base is sodium bicarbonate.

It was surprisingly found that the actual end product of one of the variants of the new synthetic route is the mono hydrate of the mono hydrochloric acid salt of 3-amino-8-(1-piperazinyl)-2H-1-benzopyran-2-one hereafter referred to as ° Compound 1'. This compound has not been described earlier and was shown to have pharmaco-chemical properties making it suitable as a drug candidate.

In a further aspect the invention therefore relates to novel salts and hydrates of salts of said compound, having the structure given by formula (7):

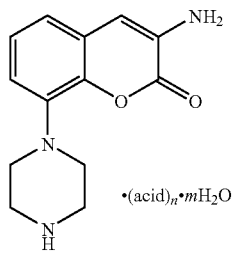

(7)

wherein '(acid)' is any acid producing pharmaceutically acceptable salts, for instance inorganic acids such as hydrochloric acid, sulphuric acid, phosphoric acid and nitric acid, or organic acids such as citric acid, fumaric acid, maleic acid, tartaric acid, acetic acid, trifluoro acetic acid, benzoic acid, p-toluene sulphonic acid, methane-sulphonic acid and naphthalene sulphonic acid, n=0, 1, 2 or 3 and m=0, 1, 2 or 3, with the proviso that when acid=HCl and n=1, m cannot be 0.

Especially preferred is the mono hydrochloric acid mono hydrate of 3-amino-8-(1-piperazinyl)-2H-1-benzopyran-2-one.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Dose

The affinity of the compounds of the invention for serotonin and other receptors was determined as described below. From the binding affinity measured for a given compound, one can estimate a theoretical lowest effective dose. At a concentration of the compound equal to twice the measured $K_i$-value, 100% of the receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight. 1-[2H-1-Benzopyran-2-one-8-yl]-piperazine derivatives, broad spectrum 5-HT receptor binding compounds, having amongst other functional serotonin receptor activities, potent $5\text{-HT}_{1A}$-agonistic as well as $5\text{-HT}_{1D}$-antagonistic activity, can be used for the treatment of affections or diseases of the central nervous system caused by disturbances of the serotonergic transmission, for example psychoses, aggression, anxiety disorders, autism, vertigo, disturbances of cognition or memory, and in particular for the treatment of depression. The presence of $5\text{-HT}_{1D}$ antagonism is of therapeutic value. $5\text{-HT}_{1D}$ receptors are located presynaptically on the nerve terminal and have a negative modulatory influence on the release of 5-HT. Therefore, blockade of these receptors enhances the release of 5-HT from its terminals. The additional presence of presynaptic $5\text{-HT}_{1D}$ antagonism will result in a similar effect as observed after administration of 5-HT reuptake inhibitors. When $5\text{-HT}_{1D}$ antagonism is combined with $5\text{-HT}_{1A}$ agonism the later activity is strengthened.

Surprisingly, these compounds as well as prodrugs and salts thereof, were found to be potently active in experimental animal models of epilepsy. The compounds are devoid of sedative effects when given in dosages up to 100 mg/kg p.o., and were also shown to be highly active as inducers of growth factors. The latter activity is indicative of neuroprotective effects and improvement of brain plasticity required for neuroregeneration, and also indicative of potential therapeutic effects in neuropathic pain (see P. Anand., "*Neurotrophic factors and their receptors in human sensory neuropathies*", Prog. Brain Res., 146, 477-492, 2004; and R. Wang et al., "*Glial cell line-derived neurotrophic factor normalizes neurochemical changes in injured dorsal root ganglion neurons and prevents the expression of experimental neuropathic pain*", Neuroscience, 121, 815-824, 2003) and diabetes induced pain (J. A. Christianson et al., "*Beneficial effects of neurotrophin treatment on diabetes-induced hypoalgesia in mice*", J. Pain, 4, 493-504, 2003).

It was also found that the compounds of the invention are active in experimental animal models with predictive value for activity against the symptoms of Parkinson's disease in particular and dyskinesias in general. Moreover, the compounds when given orally show a good bioavailability, which results in high potency and long duration of action. The unique pharmacological profile of compounds of the invention makes them particularly useful in the treatment of movement disorders, including Parkinson's disease, Huntington's Chorea, progressive supranuclear palsy, Wilson's disease, Tourette's syndrome, symptomatic and non-symptomatic epilepsy, seizures, including refractory seizures and post-stroke seizures and other electroconvulsive disorders, various chronic tremors, including essential tremor, tics and dystonias.

Surprisingly, these compounds as well as prodrugs and salts thereof, were also found to be potently active in experimental animal models of pain. The pharmacological activities as realized in the compounds of the invention and their salts represents a novel class of analgesic compounds for the treatment of chronic pain disorders or in treating other conditions where there is hyper-sensitization to painful signals, hyperalgesia, allodynia, enhanced pain perception, and enhanced memory of pain.

The following examples are only intended to further illustrate the invention, in more detail, and therefore these examples are not deemed to restrict the scope of the invention in any way.

Example I

Analytical Methods Used During Syntheses

Nuclear Magnetic Resonance (NMR) Spectroscopy

NMR spectra were recorded on a Bruker AM400 spectrometer, or a Varian VXR400S spectrometer. Chemical shifts ($\delta$) were reported in ppm downfield from TMS as internal standard. A sample of 10-50 mg was dissolved in a deuterated solvent, usually $CDCl_3$ or a DMSO-d6/$CDCl_3$ (4:1 v/v) mixture). The solvent was selected to ensure complete dissolution of the sample. The free induction decays were generally obtained at room temperature under the following conditions:

| | |
|---|---|
| Digital resolution | 0.2 Hz |
| Sweep width | 18 ppm |
| Pulse width | 20 degrees |
| Pulse repetition time | 4.5 sec or longer if required for complete relaxation |
| Carrier frequency | 6.0 ppm |
| Number of acquisitions | 128 or more if necessary. The C-13 satellite signals at 0.5% signal intensity should be clearly visible. |

NMR was used as method for determining relative contents.

Titrimetry (Chloride and Water Determinations)

For potentiometric titrations, a Metrohm model E636 (Switzerland) was used.

Potentiometric chloride determinations were used in this syntheses to determine chloride. The titration was performed with a combined silver electrode and silver nitrate titrant. The method is specific for chloride because it can distinguish chloride from iodide and bromine on basis of different electrode potentials.

Voltametric titrations for the determination according to Karl Fisher were performed using a Metrohm 633KF (Metrohm, Switzerland) apparatus according to the USP method.

Example II

Synthesis of 3-Amino-8-(1-Piperazinyl)-2H-1-Benzo-Pyran-2-One and its Monohydrochloric Acid Monohydrate (Compound 1)

Step 1: Nitration

The first step was the nitration of 5-bromo-2-hydroxybenzaldehyde (1*) yielding 5-bromo-2-hydroxy-3-nitrobenzaldehyde (2*):

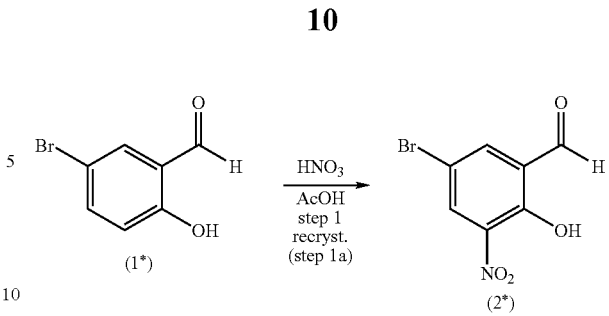

A solution of 1.0 mol of 5-bromo-2-hydroxybenzaldehyde (1*) in 3.75 litres acetic acid (98%) was formed on heating the mixture to about 60° C. 1.5 mol of concentrated nitric acid (137 g=97 ml) was added slowly in approximately 1 hour. After the completion of the addition stirring was continued at 65° C. for a further 10 minutes. The solution was then cooled to 45° C., and the product was precipitated by the addition of 4 litres of water. After stirring for at least 3 hours the product was collected on a filter and washed with water until the pH of the mother liquor was approximately 6. The material was dried as much as possible by centrifugation. The crude product was dissolved in 800 ml acetone under refluxing and stirring. 400 ml acetone was removed by distillation. After cooling to 20° C., the mixture was stirred for 3 hours. The precipitate was collected on a filter and washed with petroleum ether 40-65° C. The solid was dried overnight in an air stream at 40° C. Finally, the crude (2*) was recrystallized from acetone to yield an end product with a purity of 98% as shown by NMR analysis.

5-bromo-2-hydroxybenzaldehyde (1*) was identified by its characteristic chemical shift $\delta$ 9.84 ppm; 5-bromo-2-hydroxy-3-nitrobenzaldehyde (2*) had a characteristic chemical shift of $\delta$ 10.4 ppm.

The overall yield of this step was approximately 60% (crude on crude).

Step 2: Erlenmeyer Condensation

The second step was the Erlenmeyer condensation of 5-bromo-2-hydroxy-3-nitrobenzaldehyde (2*) with N-acetyl-glycine to yield N-(6-bromo-8-nitro-2-oxo-2H-1-benzopyran-3-yl)acetamide (3*).

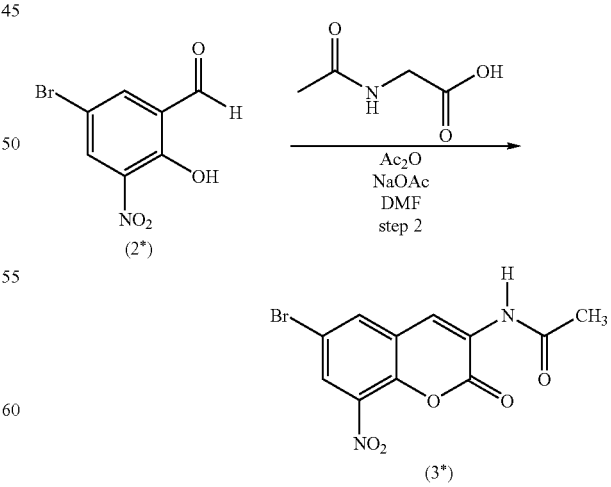

To a mixture of 1.0 mol of 5-bromo-2-hydroxy-3-nitrobenzaldehyde (2*), 1.0 mol of N-acetylglycine and 1.0 mol of anhydrous sodium acetate, 800 ml of N-methyl-2-pyrrolidone are added. The mixture was stirred and heated to 50° C. Then 2.2 mol of acetic anhydride was run into the reaction vessel in approximately 30 minutes. The reaction mixture was heated to 100° C. During heating the reacting mixture became homogeneous for a while; shortly afterwards a solid was formed, making stirring troublesome. After heating at 100° C. for 4 hours, the mixture was cooled to 80° C. and 1,100 ml of acetic acid (98%) was added. Thereafter stirring of the mixture was easy. Next, the mixture was cooled to room temperature, and stirred for 60 minutes. The precipitate was collected on a filter and washed twice with 625 ml acetic acid (80%), five times with 900 ml water, and once with 300 ml acetone. The product was dried in an air stream at 40° C. for 24 hours, and had a purity of 98% as shown by NMR analysis.

5-bromo-2-hydroxy-3-nitrobenzaldehyde (2*) had a characteristic shift of δ 10.4 ppm; the characteristic chemical shift of N-(6-bromo-8-nitro-2-oxo-2H-1-benzopyran-3-yl)acetamide (3*) was δ 8.72 ppm The overall yield of this step was approximately 80% (crude on crude).

Step 3: Reduction

The third step was the catalytic hydrogenation of N-(6-bromo-8-nitro-2-oxo-2H-1-benzopyran-3-yl)acetamide (3*) to N-(8-amino-2-oxo-2H-1-benzopyran-3-yl)-acetamide (4*).

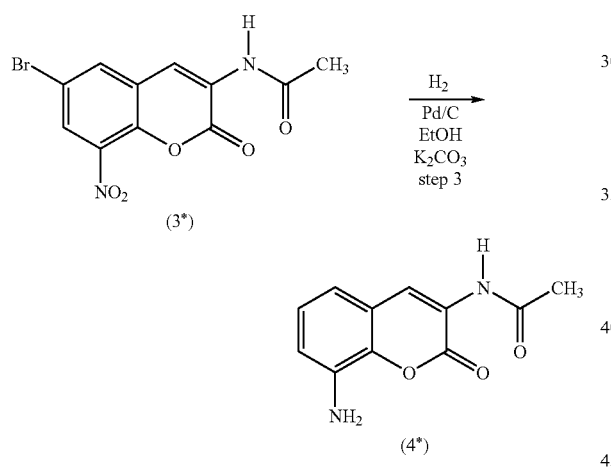

A mixture of 1.0 mol of N-(6-bromo-8-nitro-2-oxo-2H-1-benzopyran-3-yl)acetamide (3*), 50 g of 10% palladium on carbon paste (containing 61% water), 1.0 mol of potassium carbonate and 15 litre of ethanol was heated to 60° C. At this temperature the starting material was reduced with hydrogen at an overpressure of 4 bar at 1400 rpm. After completion of the reaction (1 hour), the catalyst was removed by filtration using filteraid, and washed with 4.5 litre methyl ethyl ketone (MEK). The filtrate was concentrated to 2 litre, and 2.3 litre of MEK was added In order to change the solvent from ethanol to MEK, 2 litre of the solvent mixture was distilled off at normal pressure and 2 litre of MEK was added. This was repeated 4 times. Then 5 litre of MEK and 2.6 litre of water were added and the mixture was stirred. The layers were separated. The upper later was concentrated at normal pressure to approximately 3.5 litre. The residue was cooled to 25° C. During this cooling the product crystallized. Then the mixture was cooled to −10° C. and stirred for two hours. The solid was filtered and washed three times with 800 ml hexane. The product was dried (50° C., 20 cm Hg, $N_2$) until constant weight.

N-(6-bromo-8-nitro-2-oxo-2H-1-benzopyran-3-yl)acetamide (3*) had a characteristic chemical shift of δ 8.72 ppm; that of N-(8-amino-2-oxo-2H-1-benzo-pyran-3-yl)-acetamide (4) was δ 8.55 ppm The overall yield of this step was approximately 70% (crude on crude):

Step 4: Construction of Piperazine Ring System

Step 4 was the alkylation of N-(8-amino-2-oxo-2H-1-benzopyran-3-yl)-acetamide (4*) with bis-chloroethylamine yielding N-(8-(1-piperazinyl)-2-oxo-2H-1-benzopyran-3-yl-)acetamide (5*).

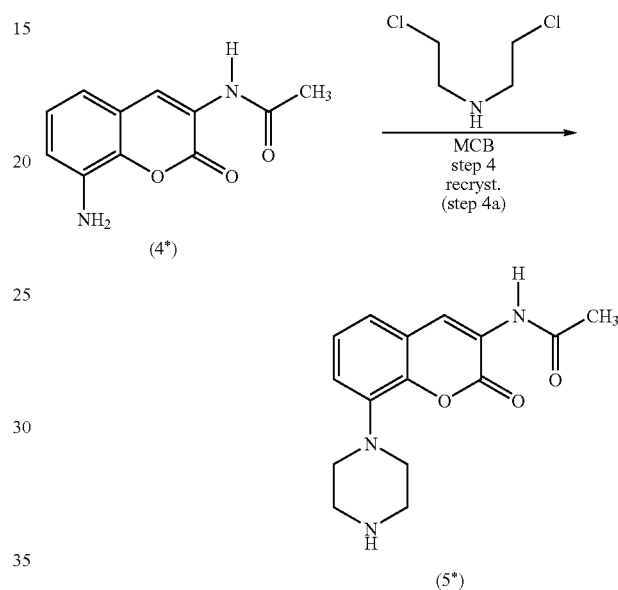

A mixture of 2.5 litre monochlorobenzene, 1.0 mol of N-(8-amino-2-oxo-2H-1-benzo-pyran-3-yl)-acetamide (4*) and 1.2 mol bischloroethylamine hydrochloride was heated to reflux under nitrogen. Part of the monochlorobenzene (0.5 litre) was distilled off. This mixture was refluxed for 10 days. The reaction was followed by HPLC. After the reaction, the mixture was cooled to 20° C. and stirred overnight. The solid product was collected on a filter and washed once with 360 ml monochlorobenzene and 3 times with 360 ml ethanol. The product was dried in vacuum at 50° C.

Half of the crude product was dissolved in 3 litre water. After addition of 18 g of Celite and 50 g of charcoal, the mixture was stirred for 1 hour at room temperature. After filtration the solution was concentrated by distillation of water. In the mean time the second half of the crude product was treated as described above. When the total volume of the combined aqueous solutions was about 1.5 litre, distillation was stopped and the mixture was cooled to room temperature. Then 125 g sodium bicarbonate was added in portions. After stirring for 1.5 hours at 15° C. the precipitate formed was collected on a filter. After washing with 360 ml water and 2 times with 270 ml ethanol, the product was dried in vacuum at 50° C.

N-(8-amino-2-oxo-2H-1-benzo-pyran-3-yl)-acetamide (4*) had a characteristic chemical shift of δ 8.55 ppm; that of N-(8-(1-piperazinyl)-2-oxo-2H-1-benzopyran-3-yl-)acetamide (5*) was δ 8.57 ppm.

The overall yield of this step was approximately 50% (crude on crude).

Step 5: Amide Hydrolysis

Step 5 was the hydrolysis of the amide function of N-(8-(1-piperazinyl)-2-oxo-2H-1-benzopyran-3-yl-)acetamide (5*) using hydrochloric acid. This resulted in the trihydrochloric acid salt of 3-amino-8-(1-piperazinyl)-2H-1-benzopyran-2-one (6*).

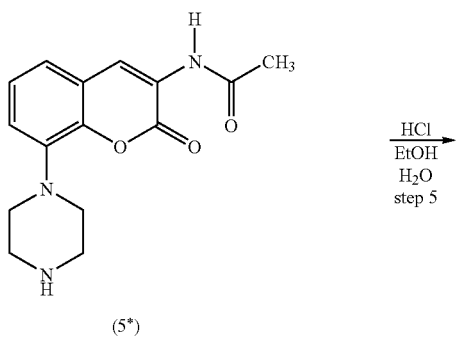

2.9 Litre of concentrated hydrochloric acid was added at room temperature to a suspension of 1.0 mol of N-(8-(1-piperazinyl)-2-oxo-2H-1-benzopyran-3-yl-)acetamide 5*) and 1.4 litre of absolute ethanol in about 10 minutes. During this addition the temperature rose to 40° C. After the addition the mixture was stirred at a temperature of 50° C. during 1.5 hours. The mixture was cooled to 20° C. and, after crystallisation had started, 1.4 litre of absolute ethanol was added. Then the mixture was stirred for 1 hour at 20° C. and for 2 hours at 0° C. The crystals were isolated by filtration and washed twice with 0.6 litre of acetone. The isolated product was dried in vacuum (40° C., 200 mm Hg, $N_2$, 24 hours).

N-(8-(1-piperazinyl)-2-oxo-2H-1-benzopyran-3-yl-)acetamide (5*) had a characteristic chemical shift of δ 8.57 ppm; the trihydrochloric acid salt of 3-amino-8-(1-piperazinyl)-2H-1-benzopyran-2-one (6*) had a characteristic chemical shift of δ 6.77 ppm.

The overall yield of this step was approximately 85% (crude on crude).

Step 6: Partial Neutralisation

The final step, the sixth, was the partial neutralisation of the trihydrochloric acid salt (6*) with sodium bicarbonate to produce the desired product: COMPOUND 1, the mono hydrochloric acid mono hydrate of 3-amino-8-(1-piperazinyl)-2H-1-benzopyran-2-one (7*)

To a suspension of 1.0 mol of the trihydrochloric acid salt (6*) in 3.5 litre ethanol a solution of 2.2 mol sodium bicarbonate in 2.8 litre water was added in about 30 minutes. The temperature was between 20° C. and 25° C. The suspension was then stirred for 3 hours. The reaction mixture was filtered and subsequently washed with 1.1 litre water, 1.1 litre ethanol and 1.1 litre hexane. The isolated crude product was dried in vacuum (40° C., 200 mm Hg, $N_2$, 24 hours).

The dried product (1 mol) was dissolved in 9 litre methanol by heating to reflux temperature. The solution did not become completely clear. After cooling to 20° C. the mixture was filtered. 300 ml of water and 150 ml of methanol was added to the filtrate, after which about 3 litre of the solvent mixture was distilled at normal pressure. The complete procedure was repeated with another quantity of 1 mol of the dried product. Then the combined fractions were concentrated to a volume of about 12 litres by distillation. After addition of 6 litre ethanol, 6 litre of the solvent mixture was removed by distillation at normal pressure. The mixture was then cooled to 0° C. and stirred for 2 hours. The precipitate was collected on a filter and washed twice with 750 ml acetone. The product was dried under vacuum (40° C., 200 mm Hg, $N_2$, 24 hours), and thereafter homogenized by milling and, when necessary, by micronizing.

The overall yield of this step was approximately 85% (crude on crude).

The trihydrochloric acid salt of 3-amino-8-(1-piperazinyl)-2H-1-benzopyran-2-one (6*) had a characteristic chemical shift of δ 6.77 ppm; that of the endproduct, COMPOUND 1, was δ 6.7 ppm. COMPOUND 1, the mono hydrochloric acid mono hydrate of 3-amino-8-(1-piperazinyl)-2H-1-benzopyran-2-one, had a molecular formula $C_{13}H_{18}ClN_3O_3$ and a molecular mass of 299.5. The pure product (99.8%, NMR) was a white to yellowish powder. Its chloride content was 11.7% (mass to mass), as determined by titrimetry. Its water content, determined by Karl Fisher. water assay titration, was 6.5% (mass to mass).

Example III

Formulation of Compound 1 as Used in Animal Studies

For oral (p.o.) administration: to the desired quantity (0.5-15 mg) of COMPOUND 1 in a glass tube, some glass beads were added and the substance was milled by vortexing for 2 minutes. After addition of 1 ml of a solution of 1% methylcellulose in water, the compound was suspended by vortexing for 10 minutes. For concentrations up and above 1 mg/ml remaining particles in the suspension were further suspended by using an ultrasonic bath.

Example IV

Receptor Binding Profile of Compound 1

The binding data collected in the table below were either obtained by CEREP (128, rue Danton, 92500 Rueil-Malmaison, France) or at Solvay Pharmaceuticals B.V., using well documented standard procedures.

RECEPTOR BINDING PROFILE OF COMPOUND 1

| receptor | $S^1$ | radioligand | $K_i$(nM) Compound 1 |
|---|---|---|---|
| $5\text{-HT}_{1A}$ | h | [$^3$H]-8-OH-DPAT | 0.25 |
| $5\text{-HT}_{1B}$ | r | [$^{125}$I]-cyanopindolol | 2.0 |
| $5\text{-HT}_{1D}$ | b | [$^3$H]-serotonin | 13 |
| $5\text{-HT}_{2A}$ | h | [$^3$H]-ketanserin | 630 |
| $5\text{-HT}_{2B}$ | h | [$^3$H]-LSD | 320 |
| $5\text{-HT}_{2C}$ | h | [$^{125}$I]-DOI | >1,000 |
| $5\text{-HT}_3$ | h | [$^3$H]-BRL 43694 | 250 |
| $5\text{-HT}_4$ | h | [$^3$H]-GR 113808 | >1,000 |
| $5\text{-HT}_5$ | h | [$^3$H]-LSD | 100 |
| $5\text{-HT}_6$ | h | [$^3$H]-LSD | >1,000 |
| $5\text{-HT}_7$ | h | [$^3$H]-LSD | 3.2 |
| $5\text{-HT}_{reuptake}$ | h | [$^3$H]-paroxetine | >1,000 |
| $\alpha_1$-adrenergic | r | [$^3$H]-prazosin | >1,000 |
| $\alpha_{1A}$-adrenergic | r | [$^3$H]-prazosin | 630 |
| $\alpha_{1B}$-adrenergic | r | [$^3$H]-prazosin | >1,000 |
| $\alpha_2$-adrenergic | r | [$^3$H]-RX 821002 | >1,000 |
| $\beta_1$-adrenergic | h | [$^3$H]-CGP 12177 | 50 |
| $\beta_2$-adrenergic | h | [$^3$H]-CGP 12177 | 40 |
| $\beta_3$-adrenergic | h | [$^{125}$I]-iodocyanopindolol | >1,000 |
| $NA_{reuptake}$ | h | [$^3$H]-nisoxetin | >1,000 |
| Dopamine-$D_1$ | h | [$^3$H]-SCH 23390 | >1,000 |
| Dopamine-$D_2$ | h | [$^3$H]-spiperone | >1,000 |
| Dopamine-$D_3$ | h | [$^3$H]-spiperone | >1,000 |
| Dopamine-$D_4$ | h | [$^3$H]-spiperone | >1,000 |
| Dopamine-$D_5$ | h | [$^3$H]-SCH 23390 | >1,000 |
| Dopamine$_{reuptake}$ | h | [$^3$H]-GBR 12935 | >1,000 |
| Muscarine-$M_1$ | h | [$^3$H]-pirenzepine | >1,000 |
| Muscarine-$M_2$ | h | [$^3$H]-AFDX-384 | >1,000 |
| Muscarine-$M_3$ | h | [$^3$H]-4-DAMP | >1,000 |
| Muscarine-$M_4$ | h | [$^3$H]-4-DAMP | >1,000 |
| Muscarine-$M_5$ | h | [$^3$H]-4-DAMP | >1,000 |
| Histamine-$H_1$ | h | [$^3$H]-pyrilamine | >1,000 |
| Histamine-$H_2$ | h | [$^{125}$I]-APT | >1,000 |
| Histamine-$H_3$ | r | [$^3$H]-$\alpha$-methylhistamine | >10,000 |
| tryptamine | r | [$^3$H]-tryptamine | >10,000 |
| melatonin | c | [$^{125}$I]-2-iodomelatonin | >10,000 |
| nicotine | r | [$^3$H]-cytisine | >10,000 |
| $\mu$-opiate | r | [$^3$H]-DAMGO | >1,000 |
| $\kappa$-opiate | r | [$^3$H]-U 69593 | >1,000 |
| $\delta$-opiate | r | [$^3$H]-DPDPE | >1,000 |
| nociceptin (ORL$_1$) | h | [$^3$H]-nociceptine | >1,000 |
| sigma | r | [$^3$H]-DTG | >1,000 |
| sigma-SG$_1$ | g | [$^3$H]-pentazocone | >1,000 |
| sigma-SG$_2$ | r | [$^3$H]-DTG | >1,000 |
| cannabinoid-CB$_1$ | h | [$^3$H]-WIN 55,212-2 | >10,000 |
| Ca$^{++}$-channel | p | [$^3$H]-fluspirilene | >10,000 |
| Ca$^{++}$-channel | r | [$^3$H]-nitrendipine | >10,000 |
| Ca$^{++}$-channel | r | [$^3$H]-diltiazem | >10,000 |
| Ca$^{++}$-channel | r | [$^{125}$I]-$\Omega$-conotoxin | >1,000 |
| Ca$^{++}$-channel | r | [$^3$H]-D-888 | 130 |
| Ca$^{++}$-channel | r | [$^3$H]-devapamil | >10,000 |
| Na$^+$-channel | r | [$^3$H]-bathrachotoxinin | >10,000 |
| K$^+$-channel | r | [$^{125}$I]-$\alpha$-dendrotoxin | >1,000 |
| K$^+$-channel | r | [$^{125}$I]-apamin | >1,000 |
| Adenosine-$A_1$ | h | [$^3$H]-DPCPX | >1,000 |
| Adenosine-$A_{2A}$ | h | [$^3$H]-CGS 21680 | >1,000 |
| Adenosine-$A_3$ | h | [$^3$H]-AB-MECA | >1,000 |
| Purine-P2X | r | [$^3$H]-ab-MeATP | >1,000 |
| GABA$_A$ | r | [$^3$H]-muscimol | >10,000 |
| GABA$_B$ | r | [$^3$H]-PK 11195 | >1,000 |
| Glycine | r | [$^3$H]-strychnine | >10,000 |
| Glycine$_{strychn.\ insens.}$ | r | [$^3$H]-MDL105519 | >10,000 |
| NMDA | r | [$^3$H]-CGS 19755 | >10,000 |
| angiotensin-AT1 | h | [$^{125}$I]-angiotensin II | >1,000 |
| angiotensin-AT2 | h | [$^{125}$I]-CPG 42112A | >1,000 |
| benzodiazepine | r | [$^3$H]-diazepam | >10,000 |
| bombesin | r | [$^{125}$I]-bombesin | >1,000 |
| bradykinin | h | [$^3$H]-bradykinin | >1,000 |
| CCK$_A$ | h | [$^3$H]-devazepide | >1,000 |
| CCK$_B$ | h | [$^3$H]-CCK8 | >1,000 |
| CCR1 | h | [$^{125}$I]-MIP-1a | >1,000 |
| CGRP | h | [$^{125}$I]-CGRPa | >1,000 |
| CRF | h | [$^{125}$I]-oCRF | >10,000 |
| Endothelin-ET$_A$ | h | [$^{125}$I]-endothelin-1 | >1,000 |
| Endothelin-ET$_B$ | h | [$^{125}$I]-endothelin-1 | >1,000 |
| Galanin-GAL$_1$ | h | [$^{125}$I]-galanin | >1,000 |
| Galanin-GAL$_2$ | h | [$^{125}$I]-galanin | >1,000 |
| Interleukine-6 | h | [$^{125}$I]-interleukine-6 | >10,000 |
| Interleukine-8 | h | [$^{125}$I]-interleukine-8 | >1,000 |
| LTB$_4$ | g | [$^3$H]-LTB$_4$ | >10,000 |
| LTD$_4$ | g | [$^3$H]-LTD$_4$ | >10,000 |
| melanocortin | h | [$^{125}$I]-NDP-a-MSH | >1,000 |
| Neurokinin-NK$_1$ | h | [$^3$H]-substance P | >1,000 |
| Neurokinin-NK$_2$ | h | [$^{125}$I]-neurokinin$_A$ | >1,000 |
| Neurokinin-NK$_3$ | h | [$^3$H]-SR 142801 | >1,000 |
| Neuropeptide Y$_1$ | h | [$^{125}$I]-PYY | >1,000 |
| Neuropeptide Y$_2$ | h | [$^{125}$I]-PYY | >1,000 |
| Neurotensin-NT$_1$ | h | [$^{125}$I]-neurotensin | >1,000 |
| PACAP | r | [$^{125}$I]-PACAP 1-27 | >1,000 |
| Prostaglandin-I$_2$ | h | [$^3$H]-iloprost | >1,000 |
| Prostaglandin-H$_2$ | h | [$^3$H]-SQ 29548 | >1,000 |
| somatostatin | m | [$^{125}$I]-somatostatin | >1,000 |
| TRH | r | [$^3$H]-TRH | >10,000 |
| Tumor necrosis f. | r | [$^{125}$I]-TNF$\alpha$ | >1,000 |
| Vasopressine-V$_{1A}$ | h | [$^3$H]-vasopressine | >1,000 |
| VIP$_1$ | h | [$^{125}$I]-VIP | >1,000 |

$S^1$: b = bovine, c = chicken, g = guinea pig, h = human, m = mouse, p = pig; r = rat.

The invention claimed is:
1. A compound of formula:

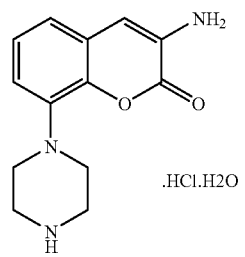

obtained by a process comprising:
(a) nitrating a compound of formula (1):

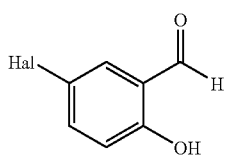

(1)

wherein Hal is F, Cl, Br, or I, to yield a 5-halogen-2-hydroxy-3-nitrobenzaldehyde of formula (2), (2)

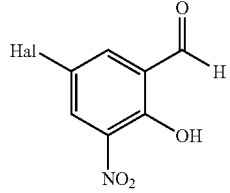

(b) subjecting (2) to an Erlenmeyer condensation with a glycine of formula

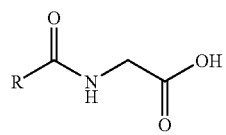

wherein R is chosen from an alkyl($C_{1-6}$) and an aryl group, to yield an N-(6-halogen-8-nitro-2-oxo-2H-1-benzopyran-3-yl) amide of formula (3), (3)

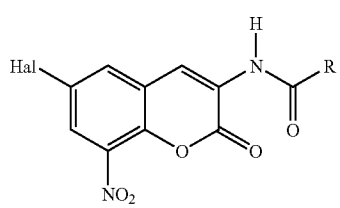

(c) subjecting (3) to a catalytic hydrogenation to yield an N-(8-amino-2-oxo-2H-1-benzopyran-3-yl) amide of formula (4), (4)

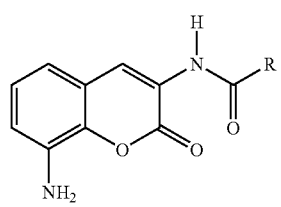

(d) alkylating (4) with a compound of the formula

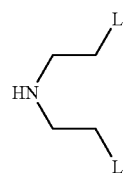

wherein L is a leaving group, to yield an N-(8-(1-piperazinyl)-2-oxo-2H-1-benzopyran-3-yl) amide of formula (5), (5)

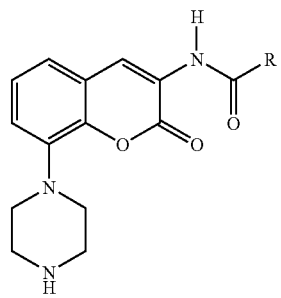

(e) hydrolyzing (5) with HCl, to yield the corresponding HCl salt (6), (6)

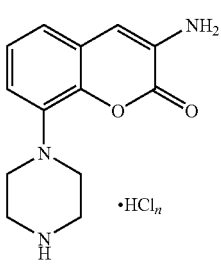

wherein n is 2 or 3, and (f) at least partially neutralizing (6) with a base to produce the compound of formula:

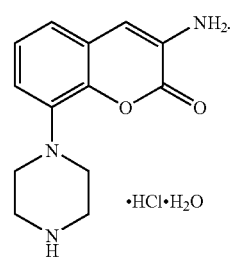

2. A hydrate of a salt of 3-amino-8-(1-piperazinyl)-2H-1-benzopyran-2-one of formula (7)

(7)

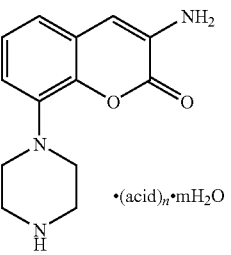

wherein the acid is chosen from organic and inorganic acids, and n* is 1 or 2, and m is 1.

3. A hydrate according to claim 2, wherein the acid is HCl.

4. A hydrate according to claim 3, wherein n* is 1, such that the compound is a mono hydrate of the mono hydrochloric acid salt of 3-amino-8-(1-piperazinyl)-2H-1-benzopyran-2-one of formula:

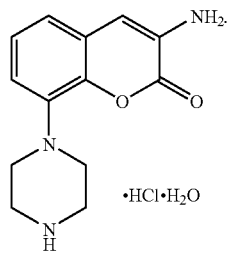

·HCl·H₂O

5. A pharmaceutical composition comprising a pharmacologically active amount of at least one compound chosen from the compounds of formula (7),

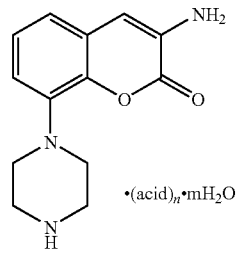

(7)

·(acid)$_{n^*}$·mH₂O and salts thereof,
wherein n* is 1 or 2, and m is 1,
and further comprising at least one component chosen from pharmaceutically acceptable carriers and pharmaceutically acceptable auxiliary substances.

6. A pharmaceutical composition according to claim 5, wherein the acid is HCl.

* * * * *

UNITED STATES PATENT AND TRADEMARK OFFICE
CERTIFICATE OF CORRECTION

PATENT NO. : 7,776,860 B2  Page 1 of 1
APPLICATION NO. : 11/085136
DATED : August 17, 2010
INVENTOR(S) : Cornelis Bakker It is certified that error appears in the above-identified patent and that said Letters Patent is hereby corrected as shown below:

On the Title page, item (57), in the Abstract, formula (7), "·(acid)$_n$·mH$_2$O" should read --.(acid)$_{n*}$.mH$_2$O--.

Claim 1, col. 16, line 50, ".HC1.H2O" should read --.HC1.H$_2$O--.

Claim 1, col. 18, line 28, "·HCl$_n$" should read --.HCL$_n$--.

Claim 1, col. 18, line 45, "·HC1·H$_2$O" should read --.HC1.H$_2$O--.

Claim 2, col. 18, line 62, "·(acid)$_{n*}$·mH$_2$O" should read --.(acid)$_{n*}$.mH$_2$O--.

Claim 4, col. 19, line 15, "HC1·H$_2$O" should read --.HC1.H$_2$O--.

Claim 5, col. 20, line 10, "·(acid)$_{n*}$·mH$_2$O" should read --.(acid)$_{n*}$.mH$_2$O--.

Signed and Sealed this

Ninth Day of November, 2010

David J. Kappos
*Director of the United States Patent and Trademark Office*